United States Patent
Yip

(10) Patent No.: US 11,189,029 B2
(45) Date of Patent: Nov. 30, 2021

(54) 3D RADIOMIC PLATFORM FOR IMAGING BIOMARKER DEVELOPMENT

(71) Applicant: TEMPUS LABS, INC., Chicago, IL (US)

(72) Inventor: Stephen Yip, Chicago, IL (US)

(73) Assignee: TEMPUS LABS, INC., Chicago, IL (US)

(*) Notice: Subject to any disclaimer, the term of this patent is extended or adjusted under 35 U.S.C. 154(b) by 99 days.

(21) Appl. No.: 16/460,975

(22) Filed: Jul. 2, 2019

(65) Prior Publication Data
US 2020/0005461 A1 Jan. 2, 2020

Related U.S. Application Data

(60) Provisional application No. 62/693,371, filed on Jul. 2, 2018.

(51) Int. Cl.
*G06T 7/00* (2017.01)
*G06T 7/60* (2017.01)
(Continued)

(52) U.S. Cl.
CPC .......... *G06T 7/0016* (2013.01); *A61B 5/4848* (2013.01); *G06T 7/10* (2017.01); *G06T 7/40* (2013.01); *G06T 7/60* (2013.01); *G06T 17/00* (2013.01); *G06T 2207/10116* (2013.01); *G06T 2207/30016* (2013.01);
(Continued)

(58) Field of Classification Search
CPC .......... G06T 7/0016; G06T 7/60; G06T 7/40; G06T 17/00; G06T 7/10; G06T 2207/10116; G06T 2207/30096; G06T 2207/30068; G06T 2207/30028; G06T 2207/30092; G06T 2207/30088; A61B 5/4848
See application file for complete search history.

(56) References Cited

U.S. PATENT DOCUMENTS

2003/0029464 A1* 2/2003 Chen ............... A61B 90/36
600/429
2005/0220807 A1* 10/2005 Lu ................... A61P 37/04
424/190.1
(Continued)

OTHER PUBLICATIONS

International Application No. PCT/US2019/040428, International Search Report and Written Opinion, dated Oct. 8, 2019.

*Primary Examiner* — Ming Y Hon
(74) *Attorney, Agent, or Firm* — Marshall, Gerstein & Borun LLP

(57) ABSTRACT

A platform is provided for generating 3D models of a tumor segmented from a series of 2D medical images and for identifying from these 3D models, radiomic features that may be used for diagnostic, prognostic, and treatment response assessment of the tumor. The radiomic features may be shape-based features, intensity-based features, textural features, and filter-based features. The radiomic features are compared to remove sufficiently redundant features, thereby producing a reduced set of radiomic features, which is then compared to separate genomic data and/or outcome data to identify clinically and biologically significant radiomic features for diagnostic, prognostic, and treatment response assessment, other applications.

31 Claims, 10 Drawing Sheets
(7 of 10 Drawing Sheet(s) Filed in Color)

(51) Int. Cl.
*G06T 7/40* (2017.01)
*G06T 17/00* (2006.01)
*A61B 5/00* (2006.01)
*G06T 7/10* (2017.01)

(52) U.S. Cl.
CPC ............... *G06T 2207/30028* (2013.01); *G06T 2207/30056* (2013.01); *G06T 2207/30061* (2013.01); *G06T 2207/30068* (2013.01); *G06T 2207/30088* (2013.01); *G06T 2207/30092* (2013.01); *G06T 2207/30096* (2013.01)

(56) References Cited

U.S. PATENT DOCUMENTS

| | | | |
|---|---|---|---|
| 2006/0093217 A1* | 5/2006 | Hong | G06T 7/0012 382/181 |
| 2009/0024028 A1* | 1/2009 | Washburn | A61B 8/5238 600/437 |
| 2009/0142337 A1* | 6/2009 | Squires | A61K 38/09 424/130.1 |
| 2013/0323301 A1* | 12/2013 | Gruber | C12N 15/867 424/450 |
| 2015/0029184 A1* | 1/2015 | Masumoto | G09B 23/30 345/419 |
| 2015/0356730 A1 | 12/2015 | Grove et al. | |
| 2017/0358079 A1* | 12/2017 | Gillies | A61B 6/032 |
| 2019/0164642 A1* | 5/2019 | Hartung | G06N 3/0454 |

* cited by examiner

3D RADIOMIC PLATFORM FOR IMAGING BIOMARKER DEVELOPMENT

CROSS-REFERENCE TO RELATED APPLICATIONS

This application claims priority to U.S. Provisional Application No. 62/693,371, filed Jul. 2, 2018, which is incorporated herein by reference in its entirety.

FIELD OF THE INVENTION

The present disclosure relates to examining medical images of a tumors and surrounding tissue and, more particularly, to developing three-dimensional models of radiomic features of the tumor for 3D image biomarker development.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Accurate assessment of treatment response provides clinicians with valuable information about the efficacy of treatment. However, current assessment techniques are often subjective and inconsistent. For many techniques, a clinician collects two-dimensional images of a tumor at different stages of treatment. The clinician then analyses the images and determines tumor growth/reduction using a one dimensional measure, i.e., tumor longest diameter. In some examples, clinicians use computer-based systems to identify tumors and track changes in tumor size using these two-dimensional images. Yet, because these conventional systems examine only two-dimensional image data, the systems, while offering a level of automation, often fail to accurately track true volumetric changes in the tumor, and thereby, they often fail to provide accurate information about treatment efficacy.

SUMMARY OF THE INVENTION

The present application presents a platform for identifying three-dimensional (3D) radiomic features for use in examining medical image data for subjects. In particular the platform may be used for identifying 3D radiomic features for developing imaging biomarker for various pathologies, including cancers. The present techniques provide a quantitative and consistent way to structure medical image data, in particular radiology data, and standardize response data collection.

The present techniques provide automated processes capable of examining large volumes of stored, digital radiology data, in an optimized manner that reduces image processing burdens and that expands diagnostic and prognostic and disease monitoring accuracy by identifying from among a large cohort of radiomic features, those particular radiomic features that are most correlative from a diagnostic and prognostic and disease monitoring viewpoint. The result is not only that large databases of radiology data may be examined to generate a reduced set of particularly important image biomarkers, but the responsiveness of tumors to treatment is more accurately assessed and in a more processing efficient manner.

As shown, the platform provides objective and standardize response assessment. The platform is able to assess target tissue and tumor imaging patterns not recognizable to clinicians examining images using the naked eye or using 2D images. Indeed, the platform is able to generate and assess entirely new imaging patterns, e.g., new 3D radiomic patterns. As such, the platform is able to identify imaging features that can improve prognosis (or clinical outcome prediction) and imaging features associated with genomic data. In these ways, the platform is able develop non-invasive imaging biomarkers for genomic data.

In accordance with an example, a computer-implemented method to analyze medical image data, the method comprises: obtaining, at one or more processors, the medical image data comprising a plurality of two-dimensional (2D) medical images; performing target tissue detection and target tissue segmentation for each 2D medical image to produce a set of segmented target tissue images; generating a three-dimensional (3D) model of detected and segmented target tissue; identifying a master set of radiomic features for the 3D model of detected and segmented target tissue; comparing at least some of the radiomic features in the master set to identify redundant radiomic features for the 3D model of detected and segmented target tissue; excluding the redundant radiomic features from the 3D model of detected and segmented target tissue; and extracting a selected set of radiomic features from the 3D model of detected and segmented target tissue.

In some examples, the target tissue is tumor tissue. In some examples, the target tissue is tumor tissue and surrounding tissue.

In some examples, the method includes identifying from among the selected set of radiomic features, radiomic features that are significantly associated with clinical outcomes and/or genomic data.

In accordance with another example, a computing device, having one or more processors is, configured to obtain, at one or more processors, the medical image data comprising a plurality of two-dimensional (2D) medical images; perform target tissue detection and target tissue segmentation for each 2D medical image to produce a set of segmented target tissue images; generate three-dimensional (3D) model of detected and segmented target tissue; identify a master set of radiomic features for the 3D model of detected and segmented target tissue; compare at least some of the radiomic features in the master set to identify redundant radiomic features for the 3D model of detected and segmented target tissue; exclude the redundant radiomic features from the 3D model of detected and segmented target tissue; and extract a selected set of radiomic features from the 3D model of detected and segmented target tissue.

In some examples, the selected set of radiomic features is analyzed to determine tumor diagnosis or prognosis.

In some examples, the selected set of radiomic features are analyzed to determine tumor treatment effectiveness, and normal tissue side effect including for example changes to the selected set of radiomic features in response to tumor treatments.

In some examples, a 3D graphic that visually depicts one or more of the selected set of radiomic features is generated and provided to medical professionals, for example, using a graphical user interface display.

In some examples, downloadable radiomic feature files, in csv (Comma-Separated Values) format, are provided to medical professionals by the system.

In some examples, downloadable segmentation files in DICOM (Digital Imaging and Communications in Medicine), nrrd (Nearly Raw Raster Data), or nifti (Neuroimaging Informatics Technology Initiative) format are also provided to medical professionals by the system.

In some examples, the selected set of radiomic features are determined by comparing a master set of radiomic features to genomic data and/or to patient treatment outcome data to identify which radiomic features within the master set of features are indicative of a tumor diagnosis, tumor prognosis, tumor treatment effectiveness, the effectiveness of treatment on normal tissues, etc.

In some examples, the radiomic features are imaging data that correlate to and are indicators of molecular or genomic data, treatment response data, diagnostic data, prognostic data, and/or classifiers of cancer patient risk stratification.

In some examples, the radiomic features are shape-based features (e.g., tumor longest diameter, 3D volume, surface area, sphericity, surface smoothness, numbers of voxels, etc.).

In some examples, the radiomic features are Intensity-based features (e.g., average tumor intensity, skewness of tumor intensity distribution, and kurtosis of tumor intensity distribution).

In some examples, the radiomic features are textural features (e.g., contrast, correlation, and homogeneity).

In some examples, the radiomic features are filter-based features (e.g., wavelets and Laplacian of Gaussian filters).

In some examples, normalization is performed on the medical images before the 3D model is generated, for example, to ensure a normalization of image intensity distribution, image color, and voxel size for the 3D model.

In some examples, the processes herein may be performed before a tumor therapy and again after a tumor therapy, or multiple times after a tumor therapy. For example a 3D model of detected and segmented target tissue may be generated from medial images taken before tumor therapy and generated again from medical images taken after the tumor therapy. A determined selected set of radiomic features from the 3D model may then be extracted and compared before tumor therapy and after tumor therapy, and the changes in each (or at least one) of the radiomic features quantified. The radiomic features compared before and after therapy may be any of those discussed herein and others, including shape-based features, intensity-based features, textural features, and filter-based features In some examples, the comparison of 3D models before and after tumor therapy, e.g., the comparison of radiomic features before and after tumor therapy, is used by a processing system to determine the efficacy of the therapy (e.g., whether there is a reduction in tumor longest diameter, 3D volume, or surface area, or a change in sphericity, surface smoothness, numbers of voxels, etc., or a change in average tumor intensity, skewness of tumor intensity distribution, or kurtosis of tumor intensity distribution, or a change in contrast, correlation, and homogeneity, or a change in wavelets and Laplacian of Gaussian filters. In some examples, that comparison data is used by a processing system to determine a next therapy or a group of matched therapies, based on the determined efficacy (e.g., based on radiomic feature significantly associated with clinical outcomes and/or genomic data and the amount of changes in those radiomic features).

BRIEF DESCRIPTION OF THE DRAWINGS

This patent or application file contains at least one drawing executed in color. Copies of this patent or patent application publication with color drawing(s) will be provided by the United States Patent and Trademark Office upon request and payment of the necessary fee.

The figures described below depict various aspects of the system and methods disclosed herein. It should be understood that each figure depicts an example of aspects of the present systems and methods.

DETAILED DESCRIPTION

Figure 1:
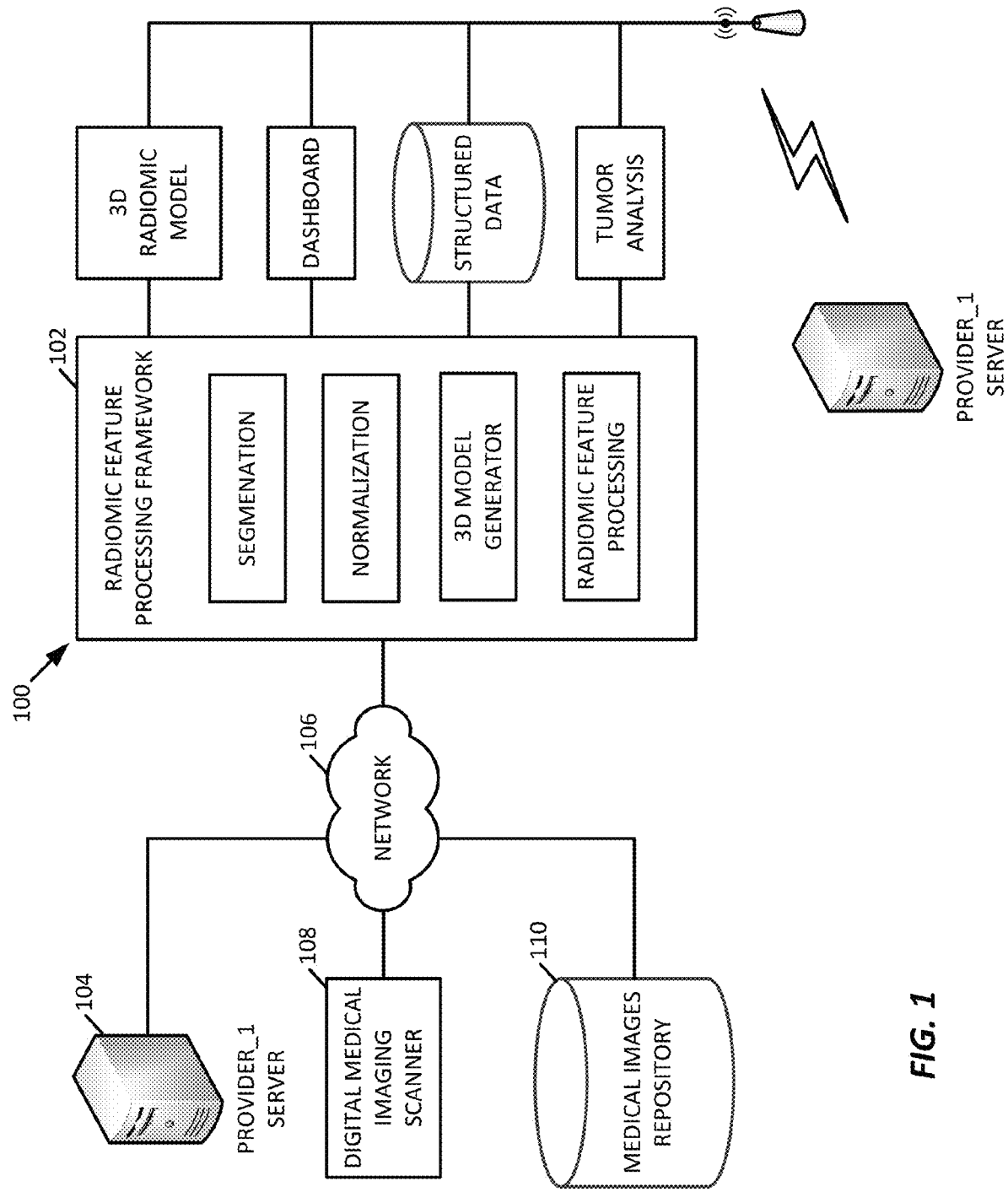
FIG. 1 is a schematic illustration of an example computer processing system for analyzing radiology images, such as tumor images (and other target tissue images), to generate a 3D model and to generate 3D radiomic features of regions of interest in the images

The present application presents a platform for identifying radiomic features for use in examining medical image data for subjects. In particular, the platform may be used for identifying radiomic features for developing imaging biomarker for various pathologies, including cancers. These radiomic features are generated from a three-dimensional (3D) model of a target tissue, where that 3D model has been generated from a series of 2D medical images.

The present techniques provide a quantitative and consistent way to structure medical image data (e.g., radiology data) and to standardize response data collection. The present techniques provide automated processes capable of examining large volumes of stored, digital radiology data, in an optimized manner that reduces image processing burdens and that expands diagnostic accuracy by identifying from among a large cohort of radiomic features, those particular radiomic features that are most correlative from a diagnostic viewpoint. The result is not only that large databases of radiology data may be examined to generate a reduced set of particularly important image biomarkers, but the responsiveness of tumors to treatment is more accurately assessed, and in shorter period of time.

The present techniques streamline the therapeutic assessment process, making the process quantitative, more objective and consistent. Furthermore, generated radiomic features can capture meaningful clinical, biological, and anisotropic changes of tumor over the course of treatment. These changes are not identifiable from traditional two-dimensional imaging and analysis and thereby provide new indicators (which we also term image biomarkers) of tumor diagnosis and prognosis. Further still, the techniques herein include segmentation and normalization techniques to generate a structure data set from numerous disparate medical image databases.

Additionally, the present techniques apply pair-wise comparisons between radiomic features to identify redundant features that may be excluded when modelling and analyzing the tumor. Redundant feature extraction can substantially reduce the computer processing resources needed to perform tumor analysis. We have found that redundant feature exclusion has been able to reduce a master radiomic feature set from numbering in the 1000s to identifying a selected group of less than 100 radiomic features and in some instances less than 10 radiomic features that may be used for diagnostic and prognostic assessment.

The tumors that may be examined by the present techniques include malignant and benign tumors. Example malignant tumors may include various cancer types, such as, breast cancer, colon cancer, gastric cancer, endometrium cancer, ovarian cancer, hepatobiliary tract cancer, urinary tract cancer, lung cancer, brain cancer, and skin cancers. The present techniques may be used to develop 3D radiomic features that correlate to any of these or other tumor types. Moreover, the present techniques may be used to develop a 3D model of radiomic features that act as 3D image biomarkers of the various tumor types. In some examples, the 3D model of radiomic features is constructed by analyzing intra-tumor radiomic features, that is, radiomic features of different tumor types within a subject or across subjects. In some examples, the 3D model of radiomic features is constructed by analyzing inter-tumor radiomic features, that is, radiomic features of the same tumor type, but appearing in different locations within a subject.

FIG. 1 illustrates a computer processing system 100 for analyzing radiology images, such as tumor images (and other target tissue images) to generate a 3D model and to generate 3D radiomic features of regions of interest in the images.

The processing system 100 includes an radiomic feature processing framework 102 communicatively coupled to a network 106 for receiving medical images and other data genomic data and drug treatment and patient outcome data. For example, the network 106 is shown coupled to a variety of different sources, from a variety of different sources, including (i) medical imaging databases of healthcare providers (Provider_1 104) such as hospitals, physician groups, labs, etc.; (ii) dedicated digital medical image scanners 108 that may be, by way of example, any suitable optical histopathology slide scanner including 20× and 40× resolution magnification scanners; (iii) medical image repositories 110 such as databases of stored medical images and (iii) the Cancer Imaging Archive (TCIA). Each of the image sources may present multiple image sources. In the illustrated example, the Provider_1 104 and the medical images repository 110 may include genomic data, treatment data, and/or patient outcome data, as desired. The processing system 100 may be coupled to other medical data sources (not shown), as well.

The medical image data herein may be any suitable two-dimensional radiology images. The radiology images may be from any suitable imaging modality, examples of which include X-ray images, computed tomography (CT) scans, magnetic resonance imaging (MRI), nuclear medicine imaging (NMR), positron-emission tomography (PET), etc.

The processing system 100 may be implemented on a computing device such as a computer, tablet or other mobile computing device, or server. The system 100 may include a number of processors, controllers or other electronic components for processing or facilitating the image capture, generation, or storage and image analysis, as described herein. An example computing device 200 for implementing processing system 100 is illustrated in FIG. 2.

Figure 2:
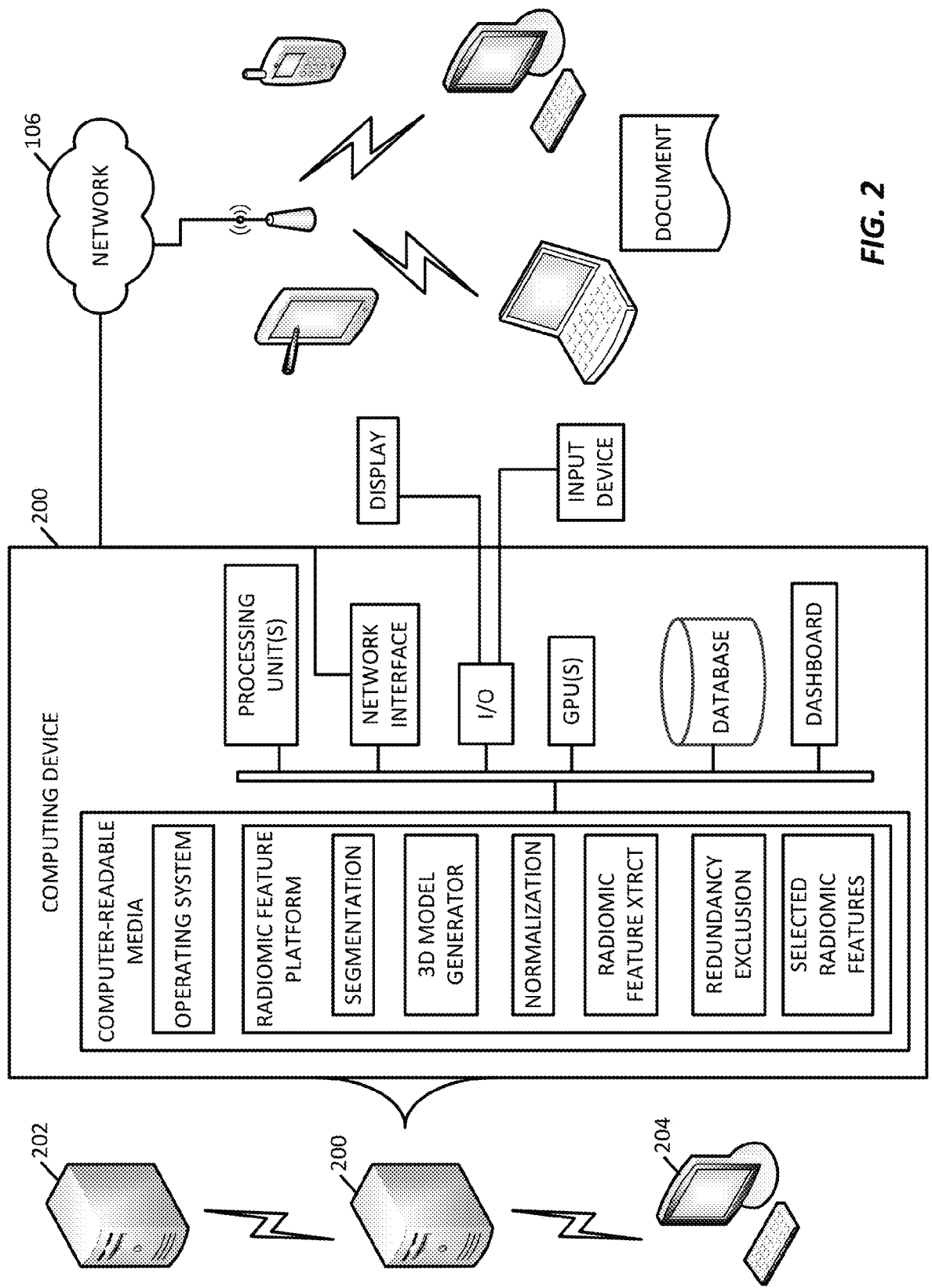
FIG. 2 illustrates an example computing device for implementing the systems of FIG. 1 and the processes of FIGS. 3, 8, and 9, in accordance with an example.

As illustrated in FIG. 2, the system 100 may be implemented on the computing device 200 and in particular on one or more processing units, which may represent Central Processing Units (CPUs), and/or on one or more or Graphical Processing Units (GPUs), including clusters of CPUs and/or GPUs. Features and functions described for the system 100 may be stored on and implemented from one or more non-transitory computer-readable media of the computing device 200. The computer-readable media may include, for example, an operating system and a radiomic feature platform corresponding to elements of the radiomic feature processing framework 102. The radiomic feature platform may include a segmentation controller, a 3D model generator, a medical image normalization controller, a radiomic feature extraction controller, a redundancy exclusion controller, and a selected radiomic features generator.

More generally, the computer-readable media may store trained 3D models, a master set of radiomic features, an identification of redundant radiomic features, and selected radiomic features.

The selected radiomic features generated by the system 100 are a subset of radiomic features optimally-defined for diagnostic and prognostic assessment of target tissue, including, for example, tumor and surrounding tissue.

These selected radiomic features may be generated from a 3D model of target tissue.

These selected radiomic features, for example, may include imaging data that correlates to and thereby indicates particular molecular data, genomic data, treatment response data, diagnostic data, prognostic data, and/or classifiers of cancer patient risk stratification. In this way, the selected radiomic features can provide imaging biomarkers.

The selected radiomic features generated by the system 100 may include: shape-based features (e.g., tumor longest diameter, 3D volume, surface area, sphericity, surface smoothness, numbers of voxels, etc.); intensity-based features (e.g., average tumor intensity, skewness of tumor intensity distribution, and kurtosis of tumor intensity distribution); textural features (e.g., contrast, correlation, and homogeneity); and filter-based features (e.g., wavelets and Laplacian of Gaussian filters).

The computing device 200 includes a network interface communicatively coupled to the network 106, for communicating to and/or from a portable personal computer, smart phone, electronic document, tablet, and/or desktop personal computer, or other computing devices. The computing device further includes an I/O interface connected to devices, such as digital displays, user input devices, etc. In the illustrated example, the processing system 100 is implemented on a single server 200. However, the functions of the system 100 may be implemented across distributed devices 200, 202, 204, etc. connected to one another through a communication link. In other examples, functionality of the system 100 may be distributed across any number of devices, including the portable personal computer, smart phone, electronic document, tablet, and desktop personal computer devices shown. The network 106 may be a public network such as the Internet, private network such as research institutions or corporations private network, or any combination thereof. Networks can include, local area network (LAN), wide area network (WAN), cellular, satellite, or other network infrastructure, whether wireless or wired. The network can utilize communications protocols, including packet-based and/or datagram-based protocols such as internet protocol (IP), transmission control protocol (TCP), user datagram protocol (UDP), or other types of protocols. Moreover, the network can include a number of devices that facilitate network communications and/or form a hardware basis for the networks, such as switches, routers, gateways, access points (such as a wireless access point as shown), firewalls, base stations, repeaters, backbone devices, etc.

The computer-readable media may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device 200 may represent a CPU-type processing unit, a GPU-type processing unit, a field-programmable gate array (FPGA), another class of digital signal processor (DSP), or other hardware logic components that can be driven by a CPU.

Returning to FIG. 1, the radiomic feature processing framework 102 includes a segmentation module that automatically identifies target tissue, such as tumors, in received medical images, segments that target tissue for analysis by the framework 102. In some examples, the segmentation module may implement a convolutional neural network to perform whole slide image segmentation. More generally, any number of unsupervised or supervised methods of image segmentation may be used. The segmentation module may be configured to perform segmentation on each 2D medical image, thereby removing from the image and retaining those portions corresponding to the target tissue, e.g., tumor. The segmentation may be patch segmentation, in which groups of pixels are examined to identify the target tissue within the medical image. For example, a segmentation process may identify a particular geometric patch that will be used for analyzing image data. Patches may be geometric, e.g., a repeating pattern of square or rectangular pixels defined across each medical image and at a pixel size sufficient to analyze changes in topology and morphology in medical images. Example patch sizes include 256×256 pixels, although fewer pixels can be used, such as 90×90, 80×80, 70×70, 60×60, 50×50, and so on, down to at least 10×10, and even further, such as 5×5 depending on the application. In other examples, patch type may be non-geometric, also termed herein a "super pixel," where each patch is allowed to vary in shape, but where the super pixels are generated to include a sufficient threshold of imaging information for topology and morphology analysis.

A normalization module normalizes the segmented image data. The normalization may normalize pixel or voxel intensity, pixel or voxel color, or other factors. The normalization module may normalize medical images from different medical image sources, thereby allowing uniform analysis across a large combined database of medical images. In some configurations, the normalization module is configured to normalize medical image data across different imaging modalities, for example, normalizing segmented X-Ray image data with segmented MRI data.

The normalization module may perform normalization on 2D medical images, in some examples. While in other examples, the normalization module may perform normalization on a 3D model generated by the framework 102, as described herein.

A 3D model generator module of the framework 102 stores the segmented and normalized image data and performs registration and data stacking processes to construct a 3D model of the target tissue or tumor. A radiomic feature processing module analyses the resulting 3D model and identifies radiomic features from that 3D model, redundant radiomic features for exclusion, and a resulting subset of clinically and biologically meaningful radiomic features (also termed diagnostic radiomic features) that can be used to diagnose tumors and/or indicate tumor state.

Figure 3:
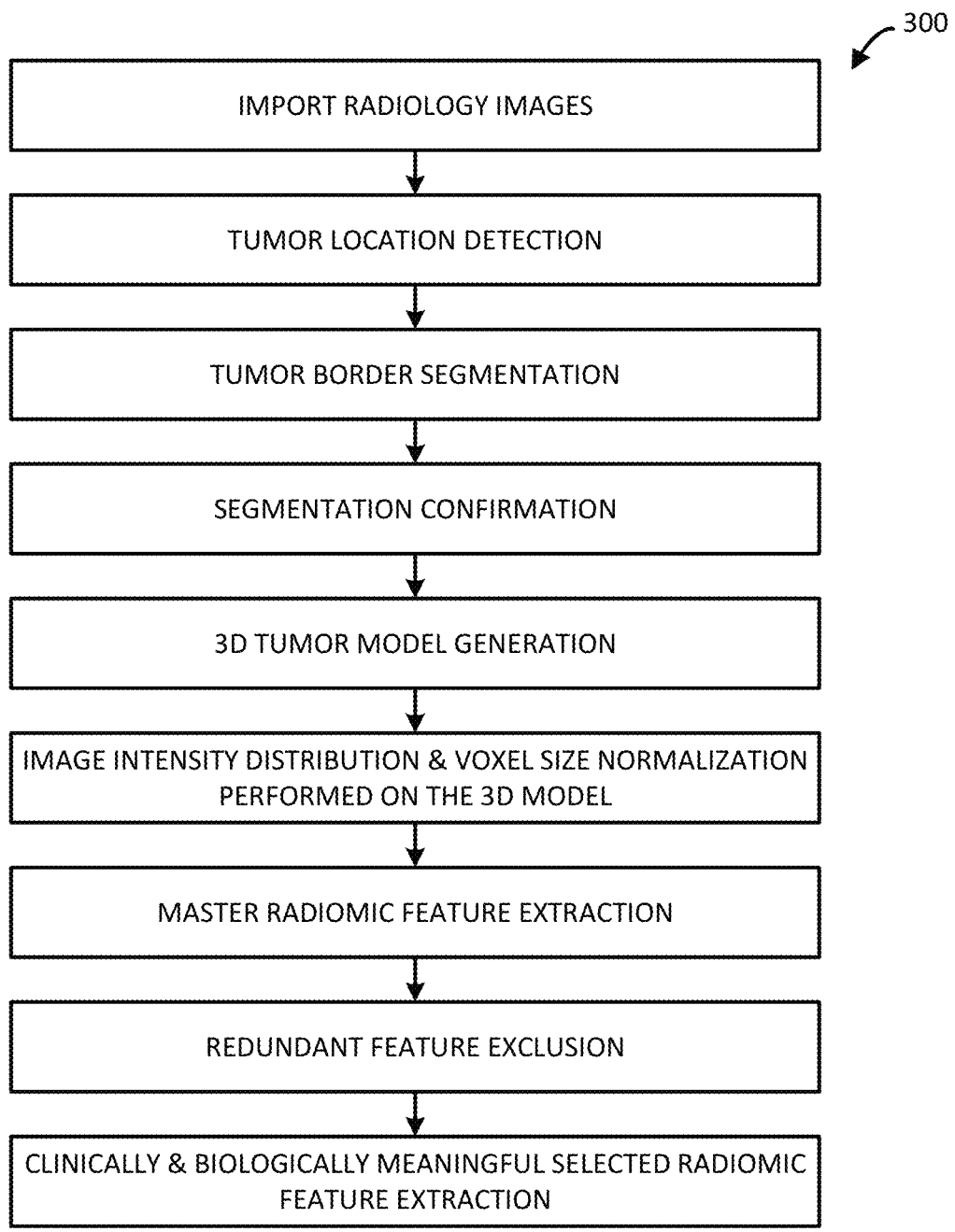
FIG. 3 is a block diagram of an example method for performing 3D radiomic feature generation and analysis on radiology images, as may be performed by the processing system of FIG. 1 and/or the computing device of FIG. 2, in accordance with an example.

FIG. 3 illustrates a process 300 for performing radiomic feature generation and analysis on radiology images, as may be performed by the processing system 100, e.g., as implemented by the computing device 200. Radiology images from image sources are imported and tumor location detection is performed. In an example automated configuration, tumor location detection is performed by comparing received radiology images to a database of tumor-identified medical images, e.g., through the use of a convolution neural network. The convolution neural network may be trained by clinical and/or synthetic training medical images, including medical images of tissue samples corresponding to the tumor to be detected, of tissue samples that do not exhibit the tumor to be detected, of tissue samples that exhibit other tumor types, and/or tissue samples exhibiting no tumor. It is noted, that in a 2D medical image, the process 300 may identify a number of different locations of tumors, as well as any number of different tumor types that may be present in the 2D medical image.

While the process 300 is discussed in reference to the particular example of tumor location detection, more broadly, the process 300 may be used to identify any target tissue. In some examples, that target tissue may encompass a tumor and surrounding tissue. In other examples, the target tissue may be any tissue imaged in the 2D images, such as organ tissue or bone tissue. That is, the segmentation, normalization, 3D modelling, and other processes described herein as applied to tumor regions may be applied to any target tissue under examination.

With the tumor location detection complete, tumor border segmentation may be achieved, for example, using an edge detection based segmentation technique. The tumor or tumor regions in the medical image are segmented out and a segmentation confirmation process may be optionally implemented. Segmentation confirmation may include, for example, assessing the shape of the tumor border to identify any regions of large shifts in intensity pixel to pixel that may indicate an improper segmentation. Segmentation confirmation may be based on the number of such regions of large shift across the entire image or across a portion of the image, for example. If the segmentation confirmation is returned as below a threshold confirmation level, then the process may repeat, until a sufficiently accurate segmentation has been achieved.

Each segmented medical image is a 2D image of a tumor, or target tissue. The segmented medical images are buffered and stored by a 3D tumor model generator that constructs a 3D model from the segmented 2D images.

In some examples, image intensity distribution and voxel size normalization is performed on the 3D model to provide uniform information across the 3D model for radiomic feature extraction. As discussed herein, such normalization allows for compensating in differences between different medical image sources (such as different medical imaging scanners), as well as across entirely different medical imaging modalities.

Figure 4:
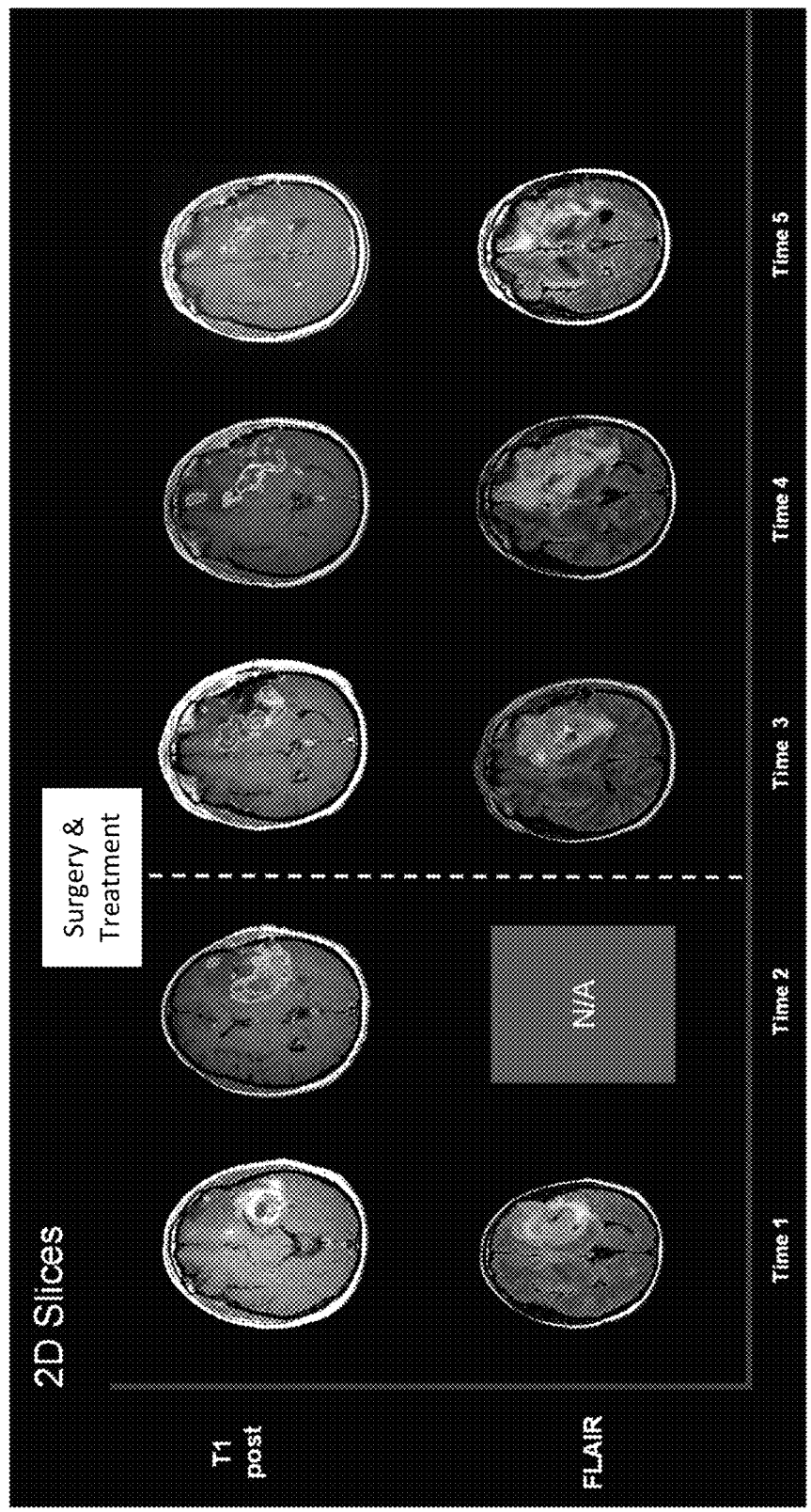
FIG. 4 illustrates 2D medical images of a portion of a tumor taken at different times in the process of treating a subject.

FIG. 4 illustrates example 2D medical image data provided to the process 300 and comprising 2D MRI images of a brain scan taken at five (5), different points in time. Time1 and Time2 are pre-treatment scans. Brain tumors are identified in the medical images. Time3-Time5 are medical images taken after surgery to remove a portion of the brain tumor and show the regression of tumor in response to therapy. FIG. 4 illustrates 2D T1 structure images and 2D T2 FLAIR (fluid attenuated inversion recovery) images, either or both of which may be provided to the process 300.

Figure 5:
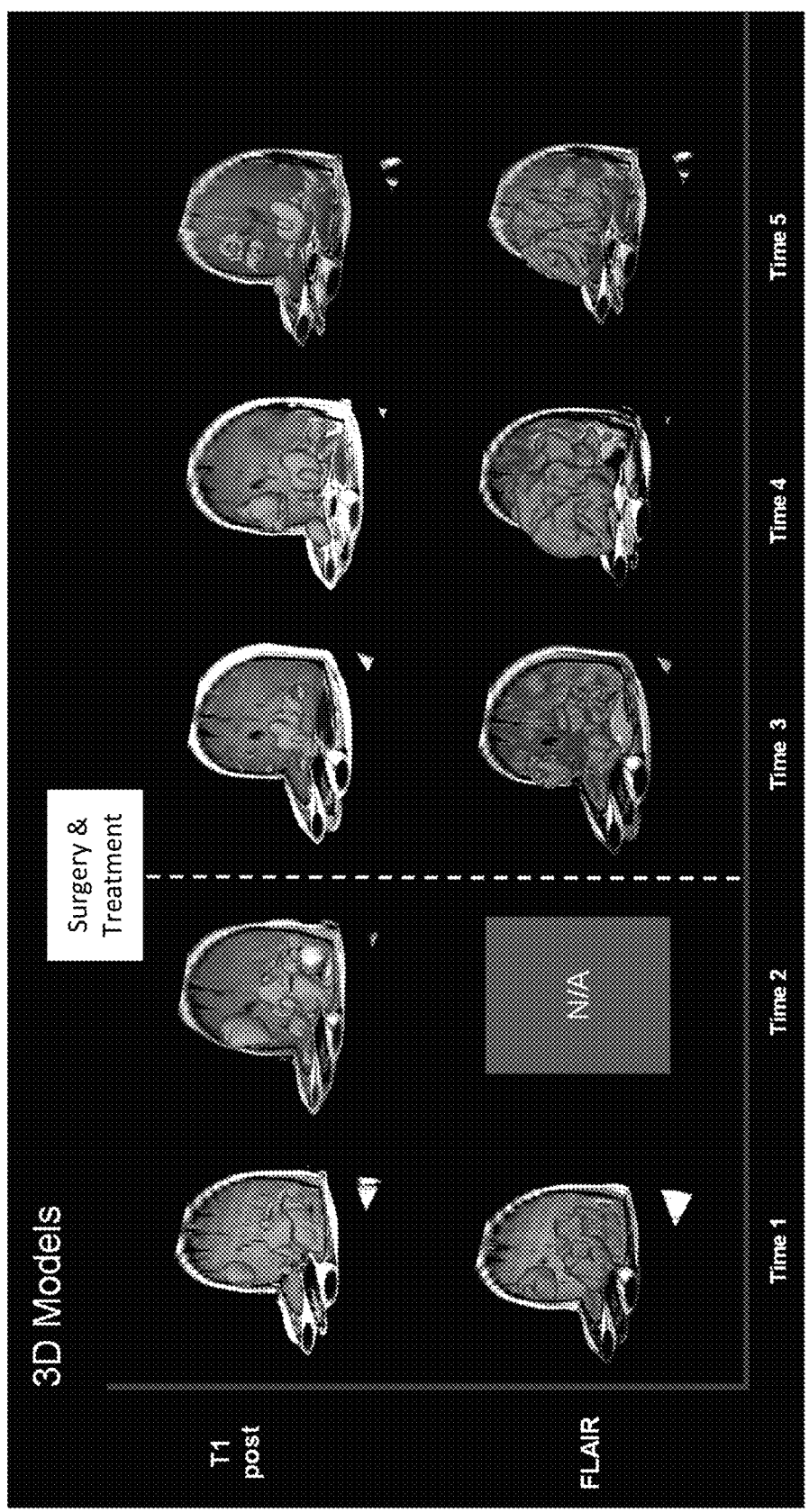
FIG. 5 illustrates 3D models of a tumor for a patient generated from 2D medical images taken at the different times of FIG. 4.

FIG. 5 illustrates example 3D models generated for each of the different image capture times of FIG. 4, where the 3D models have been generated by the process 300 from multiple 2D images taken at each time, Time1-Time5.

Returning to FIG. 3, with the 3D model normalized, a master set of radiomic features are extracted from the 3D model. The radiomic features may include, by way of example, shape-based features (e.g., tumor longest diameter, 3D volume, surface area, sphericity, surface smoothness, numbers of voxels, etc.), intensity-based features (e.g., average tumor intensity, skewness of tumor intensity distribution, and kurtosis of tumor intensity distribution), textural features (e.g., contrast, correlation, and homogeneity); and filter-based features (e.g., wavelets and Laplacian of Gaussian filters).

Figure 6:
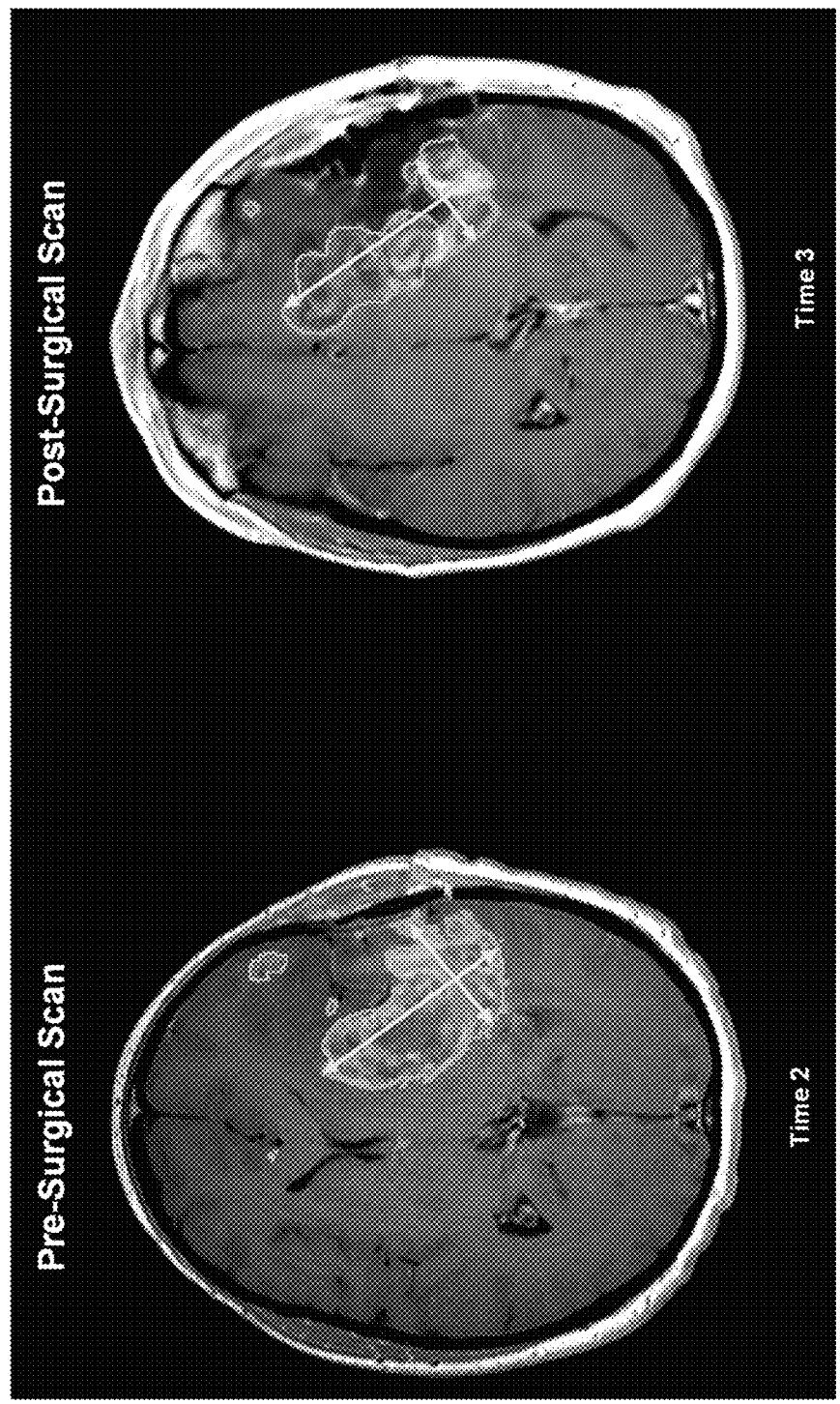
FIG. 6 illustrates 2D medical images taken of a portion of a tumor showing inconclusive differences in 2D features, such as major and minor axes.

An example radiomic feature that may be extracted from the 3D model is the tumor 3D volume. FIG. 6 shows a 2D medical image of the tumor showing major and minor (i.e., long and short) axes of the tumor region, at Time2, before surgery, and at Time3, after surgery. As indicated, just looking at this 2D image and examining for changes in the major or minor axes is inconclusive. This 2D image alone does not sufficiently instruct a clinician on the successfulness of the surgery.

Figure 7:
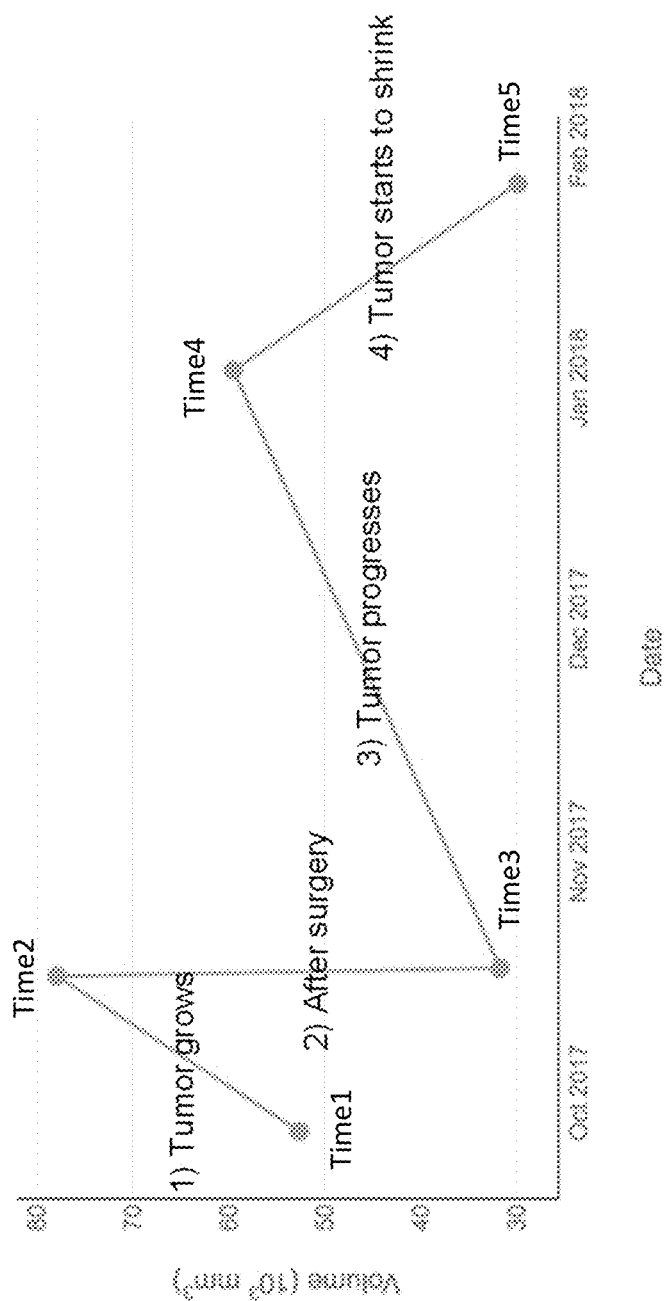
FIG. 7 is a plot of the changes in a 3D radiomic feature (e.g., tumor volume) developed from the 3D models of FIG. 5, illustrating a clear correlation between changes in the 3D radiomic feature and treatment stages.

In contrast, when we examined the tumor 3D volume radiomic feature generated from the process 300, a clear difference in volume was shown. FIG. 7 plots the measures of the tumor 3D volume radiomic feature, as a function of time, in an example. The change in 3D volume clearly correlates with surgery. Indeed, changes in the 3D volume radiomic feature of the tumor further correlated with subsequent, post-surgery treatment. These indications from the 3D volume stand in stark contrast to the inconclusive results using 2D medical image data only (i.e., FIG. 6). In other examples, changes in radiomic features may be compared before and after other kinds of treatment events. For example, the tumor 3D volume radiomic feature generated from the process 300 may be generated before a patient receives a therapy and again after a patient receives a therapy. As another example, the tumor 3D volume radiomic feature generated from the process 300 may be generated more than once after a patient receives a therapy. Exemplary therapies include chemotherapy, radiation, immunotherapy, PARP inhibitors, CAR T-cell therapy, and cancer vaccines, among other therapies. In an example, the tumor 3D volume radiomic feature generated from the process 300 may be generated in the first 60 days after receipt of a therapy. In some examples, the tumor 3D volume radiomic feature generated from the process 300 that is generated after receipt of a therapy may be utilized to determine the efficacy of the therapy. In some examples, the tumor 3D volume radiomic feature generated from the process 300 may be utilized to determine a next therapy.

Figure 8:
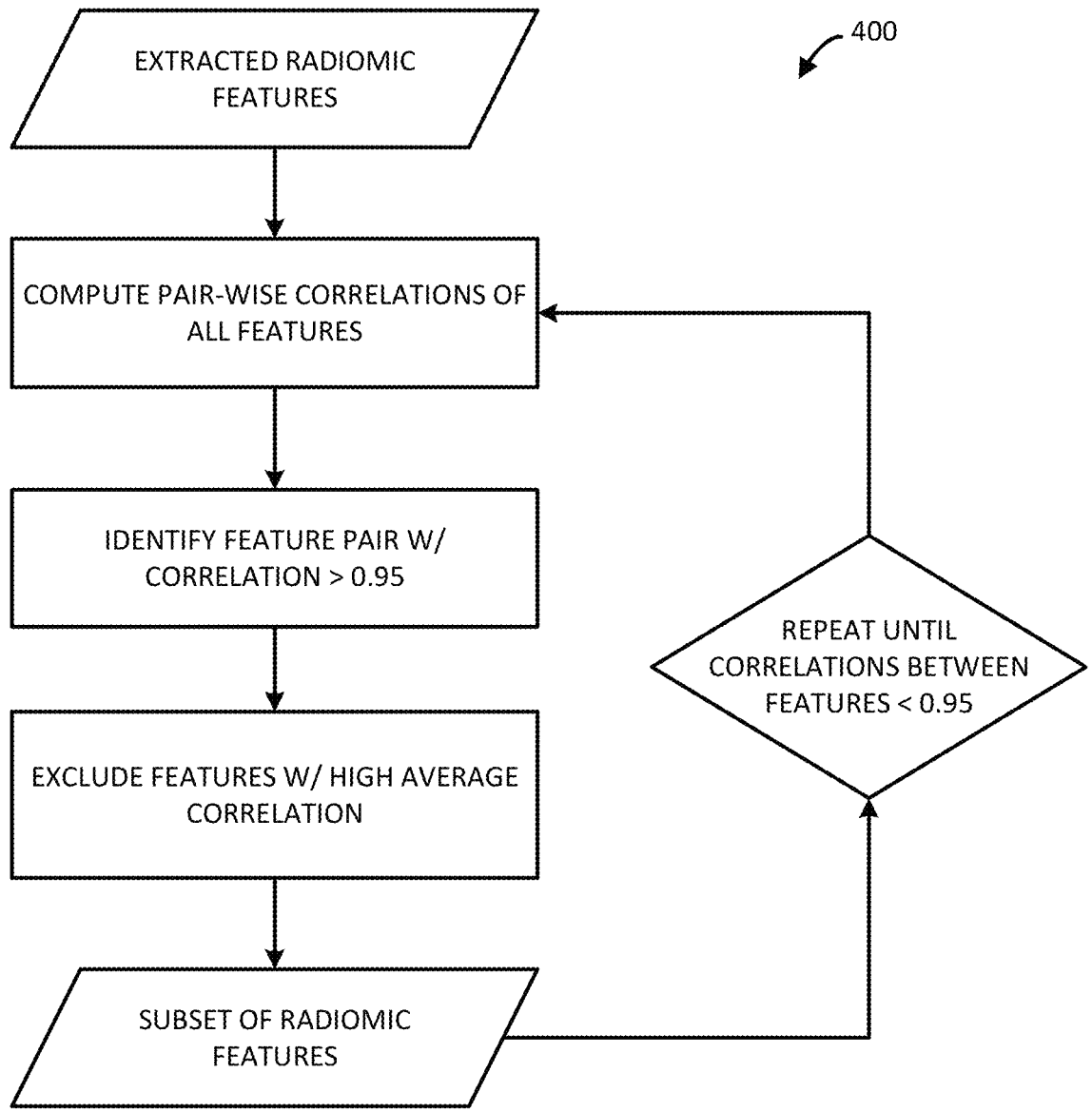
FIG. 8 is a block diagram of an example process for redundant radiomic feature identification and exclusion, as may be implemented by the method of FIG. 3, in accordance with an example.
Figure 9:
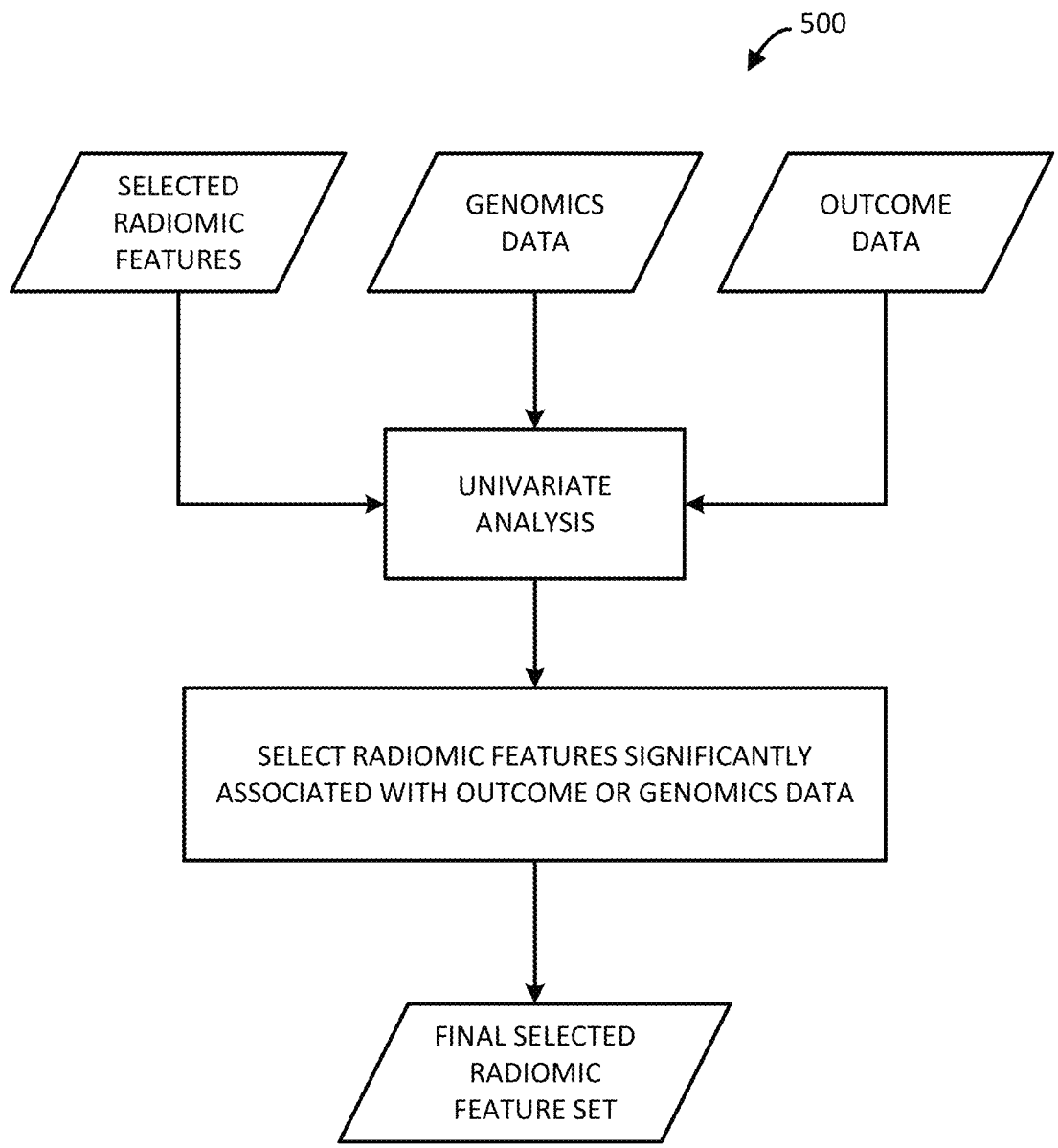
FIG. 9 is a block diagram of an example process for identification of a diagnostic radiomic feature set, as may be implemented by the method of FIG. 3, in accordance with an example.

Returning to FIG. 3, the process 300 further includes a redundant radiomic feature exclusion process, discussed in further detail in the example implementation of FIG. 8, and a diagnostic radiomic feature extraction process, discussed in further detail in the example implementation of FIG. 9.

FIG. 8 illustrates a process 400 for identifying redundant radiomic features from among a master set of radiomic features identified in the process 300. The master set of extracted radiomic features (e.g., 500, 1000, 2000, or more) is provided. For each of the features in the master set, pair-wise correlations are determined for each other of the features in the master set. The pair-wise correlations are scored and any correlations with a score above a threshold value (e.g., correlations>0.95) are identified, correlation scores are tallied for the radiomic features. Those radiomic features with a high average correlation score are removed from the masters set to generate a selected radiomic features set. The process then repeats another round until the radiomic features that are left are features that have pair-wise correlations below the threshold (e.g., <0.95). After the final round, a subset of radiomic features is produced by the process 400.

In FIG. 9, a process 500 obtains the subset of radiomic features from process 400 and determines a further subset of radiomic features, in particular, a selected radiomic feature set that may be used for diagnostic or prognostic assessments, for example to assess tumor type, treatment efficacy, etc.

In an example implementation of the process 500, the radiomic features, genomics data corresponding to the obtained medical images, and patient treatment outcome data are provided to a univariate analysis processor. The analysis processor compares each of the radiomic features obtained from the process 400 to categorized genomics data and/or to categorized outcome data. This comparison is done across a large database of medical images and 3D models. The process 500 determines, from the large database comparisons, whether any (and which) of the radiomic features are significantly associated with either genomics data or outcome data, and those significant associations are stored in a database format to identify the radiomic feature and the associations of that feature. The radiomic features identified as having significant associations are then determined to be clinically and/or biologically significant and are stored as a selected radiomic feature set. The process 500 may then generate an enhanced 3D model exhibiting only the radiomic features identified as having significant associations. In some examples, radiomic features having significant associations may be illustrated in the previously generated 3D model (3D tumor model generation process of FIG. 3) using a segmentation and color coding to visually indicate those radiomic features. In some examples, the process 500 generates a digital report or data file that includes a listing of the radiomic features having significant associations, a scoring of the level of significance (e.g., a p-value) and the associated clinical data and/or biological data. In some examples, the significant associations are covariant, in which case the report will include covariant associations.

As used herein "significant associations" refers to statistically significant associations, assessed using a statistical model such as a survival function analysis. Example statistical models include a log-rank test model or a Kaplan-Meier model. Others statistical models include a likelihood ratio test or a Wald test. Yet, in some examples herein, including FIG. 10 discussed below, a regression model that allows for covariant analysis is used, such as the Cox proportional hazards regression analysis. As used herein significant associations, resulting from the model used, refers to associations having a p-value of <0.05, <0.045, <0.040, <0.035, <0.030, <0.025, <0.020, <0.015, <0.010, <0.005, or <0.001.

Figure 10:
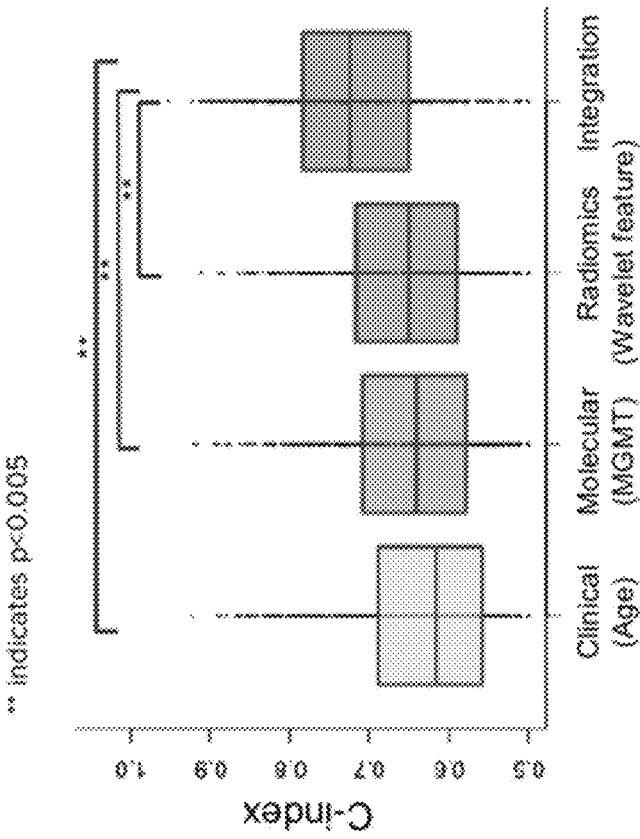
FIG. 10 is a plot showing of c-index (concordance) of clinical data, molecular data, and radiomic feature data for an example implementation. As shown, integrating radiomic feature data developed herein, with clinical and molecular data shows an increase in predictive power (i.e., a higher c-index) of outcome data.

As shown in FIG. 10, the radiomic feature data developed by the process 300 may be combined with clinical data (e.g., age in the illustrated example) and molecular data (e.g., MGMT methylation) to produce an integrated radiomic-based indicator. This integrated radiomic-based indicator can provide significantly improved c-index (Cox index of a Cox proportional hazards) values for assessing tumor and other target tissue (in the illustrated example, the c-index values shown all exhibit a p-value <0.005). That is, while radiomic features alone can serve as imaging biomarkers, in some cases, radiomic features may be combined with other data to provide even more accurate integrated imaging biomarkers. FIG. 10 is a plot showing c-index (concordance) for clinical data, molecular data, and radiomic feature data, in an example. Integrating these data sets together, e.g., through multivariate Cox proportional hazards model, results in a substantially higher c-index, which can serve as a more accurate imaging biomarker. Molecular data may include gene expression irregularities, irregular microRNA profile, splice variations, DNA methylation, etc.

Further still, the selected radiomic features may be cross-correlated against clinical outcome data and genomic data to identify significant associations. Clinical outcome data would include stored data on disease-free survival, tumor stage, response rate to particular therapeutics, absence of disease, quality of life, etc. Genomic data may include variations in DNA structure or sequence, or copy number, etc. These data types may be stored in and received from databases, such as electronic medical images databases/repositories, medical provider electronic databases, and the like.

It is noted herein, the processing comparisons and analyses may be implemented through trained or untrained processing techniques. For example, 2D image segmentation, 3D model normalization, redundant radiomic feature exclusion, pair-wise correlations, and determinations of diagnostic radiomic features may be achieved using a deep learning framework or a plurality of deep learning frameworks, such as one for each process. Broadly speaking, the deep learning framework may implement any suitable statistical model (e.g., a neural network or other model implemented through a machine learning process) that will be applied to each of the received images and other data (e.g., genomic and outcome data). As discussed herein, that statistical model may be implemented in a variety of manners. In some examples, machine learning is used to evaluate training images and develop classifiers that correlate predetermined image features to specific categories. For example, image features can be identified as training classifiers using a learning algorithm such as Neural Network, Support Vector Machine (SVM) or other machine learning process. Once classifiers within the statistical model are adequately trained with a series of training images, the statistical model may be employed in real time to analyze subsequent images provided as input to the statistical model for identifying radiomic features and correlations. In some examples, when statistical model implemented using a neural network, the neural network may be configured in a variety of ways. In some examples, the neural network may be a deep neural network and/or a convolutional neural network. In some examples, the neural network can be a distributed and scalable neural network. The neural network may be customized in a variety of manners, including providing a specific top layer such as but not limited to a logistics regression top layer. A convolutional neural network can be considered as a neural network that contains sets of nodes with tied parameters. A deep convolutional neural network can be considered as having a stacked structure with a plurality of layers. The neural network or other machine learning processes may include many different sizes, numbers of layers and levels of connectedness. Some layers can correspond to stacked convolutional layers (optionally followed by contrast normalization and max-pooling) followed by one or more fully-connected layers. For neural networks trained by large datasets, the number of layers and layer size can be increased by using dropout to address the potential problem of overfitting. In some instances, a neural network can be designed to forego the use of fully connected upper layers at the top of the network. By forcing the network to go through dimensionality reduction in middle layers, a neural network model can be designed that is quite deep, while dramatically reducing the number of learned parameters.

The 3D models, master set of radiomic features, selected set of radiomic features, and correlations and significant associations determined herein may then be visually indicated to a user, for example Provider_1, through a dashboard graphical user interface provided to a computer monitor or other display.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. A computer-implemented method to analyze medical image data, the method comprising:
   obtaining, using one or more processors, the medical image data comprising a plurality of two-dimensional (2D) medical images;
   performing, using the one or more processors, target tissue detection and target tissue segmentation for each 2D medical image to produce a set of segmented target tissue images;
   generating, using the one or more processors, a three-dimensional (3D) model of detected and segmented target tissue;
   identifying, using the one or more processors, a master set of 3D radiomic features for the 3D model of detected and segmented target tissue;
   identifying, using the one or more processors, 2D radiomic features of the 2D medical image, wherein the 2D radiomic features are different from the 3D radiomic features;
   comparing, using the one or more processors, at least some of the 3D radiomic features in the master set of 3D radiomic features and at least some of the 2D radiomic features to identify redundant radiomic features for the 3D model of detected and segmented target tissue;
   in response to the comparison, excluding, using the one or more processors, the redundant radiomic features from the 3D model of detected and segmented target tissue; and
   extracting, using the one or more processors, a selected set of radiomic features from the 3D model of detected and segmented target tissue.

2. The method of claim 1, wherein the target tissue is tumor tissue.

3. The method of claim 2, wherein the tumor tissue comprises breast cancer tissue, colon cancer tissue, gastric cancer tissue, endometrium cancer tissue, ovarian cancer tissue, hepatobiliary tract cancer tissue, urinary tract cancer tissue, lung cancer tissue, brain cancer tissue, or skin cancer tissue.

4. The method of claim 1, wherein the target tissue is tumor tissue and surrounding tissue.

5. The method of claim 1, further comprising:
   identifying from among the selected set of radiomic features, radiomic features that are significantly associated with clinical outcomes and/or genomic data.

6. The method of claim 5, further comprising:
   identifying from among the selected set of radiomic features, the radiomic features that are significantly associated with clinical outcomes and/or genomic data using a Cox proportional hazards model.

7. The method of claim 6, wherein the radiomic features significantly associated with clinical outcomes and/or genomic data have a p-value <0.005 using the Cox proportional hazards model.

8. The method of claim 6, wherein the radiomic features are shape-based features.

9. The method of claim 6, wherein the radiomic features are intensity-based features.

10. The method of claim 6, wherein the radiomic features are textural features.

11. The method of claim 6, wherein the radiomic features are filter-based features.

12. The method of claim 1, further comprising identify redundant radiomic features of the 3D model using a pair-wise comparison.

13. The method of claim 1, further comprising:
    performing the method of claim 1 (i) at a first time period before a tumor therapy and again (ii) at a second time period after the tumor therapy.

14. The method of claim 13, further comprising:
    determining changes in radiomic features from the first time period before the tumor therapy to the second time period after the tumor therapy.

15. The method of claim 14, wherein the therapy is a chemotherapy.

16. The method of claim 14, wherein the therapy is a radiation.

17. The method of claim 14, wherein the therapy is an immunotherapy.

18. The method of claim 14, wherein the therapy is a poly ADP ribose polymerase (PARP) inhibitors therapy.

19. The method of claim 14, wherein the therapy is a CAR T-cell therapy.

20. The method of claim 14, wherein the therapy is a cancer vaccine.

21. The method of claim 14, further comprising: determining efficacy of the therapy from the changes in radiomic features from the first time period before the tumor therapy to the second time period after the tumor therapy.

22. The method of claim 21, further comprising: determining a next therapy in response to determining the efficacy of the therapy.

23. A computer-implemented method for generating radiomic features for use in a 3D model of a tumor, the method comprising:
    performing, using the one or more processors, using a convolution neural network, model target tissue detection and target tissue segmentation for a plurality of 2D medical images to produce a set of segmented target tissue images;
    generating, using the one or more processors, a 3D model of detected and segmented target tissue from a plurality of 2D medical images;
    identifying, using the one or more processors, using a convolution neural network, a master set of 3D radiomic features for the 3D model of detected and segmented target tissue;
    identifying, using the one or more processors, 2D radiomic features of the 2D medical image, wherein the 2D radiomic features are different from the 3D radiomic features;
    identifying, using the one or more processors, using a statistical model comparing the 3D radiomic features and the 2D radiomic features, radiomic features from the 3D radiomic features that are significantly associated with clinical outcomes and/or genomic data; and
    storing or displaying the significantly associated radiomic features in an enhanced 3D model or in a digital report.

24. A computing device comprising:
    one or more processors;
    a user interface; and a computer-readable memory coupled to the one or more processors, the memory storing instructions that cause the one or more processors to:

perform target tissue detection and target tissue segmentation for each of a plurality of 2D medical image and produce a set of segmented target tissue images;

generate a 3D model of detected and segmented target tissue;

identify a master set of 3D radiomic features for the 3D model of detected and segmented target tissue;

identifying, using the one or more processors, 2D radiomic features of the 2D medical image, wherein the 2D radiomic features are different from the 3D radiomic features;

compare at least some of the 3D radiomic features in the master set of 3D radiomic features and at least some of the 2D radiomic features to identify redundant radiomic features for the 3D model of detected and segmented target tissue;

exclude the redundant radiomic features from the 3D model of detected and segmented target tissue;

extract a selected set of radiomic features from the 3D model of detected and segmented target tissue; and store or display the extracted set of radiomic features in an enhanced 3D model or in a digital report.

25. The computing device of claim 24, wherein the memory stores instructions that cause the one or more processors to: analyze the selected set of radiomic features and identify from the selected set of radiomic features, radiomic features that are significantly associated with clinical outcomes and/or genomic data.

26. The computing device of claim 25, wherein the memory stores instructions that cause the one or more processors to: identify the significantly associated radiomic features using a Cox proportional hazards model, wherein the significantly associated radiomic features have a p-value <0.005.

27. The computing device of claim 25, wherein the memory stores instructions that cause the one or more processors to: identify the significantly associated radiomic features correlated to tumor treatment effectiveness.

28. A computer-implemented method to analyze medical image data, the method comprising:

obtaining, using one or more processors, a first plurality of 2D medical images captured at a first time period, performing, using the one or more processors, target tissue detection and target tissue segmentation on each of the first plurality of 2D medical images to produce a set of segmented target tissue images, and generating, using the one or more processors, a first 3D model of detected and segmented target tissue;

identifying, using the one or more processors, set of 3D radiomic features in the first 3D model;

identifying, using the one or more processors, a set of 2D features in the first plurality of 2D medical images, wherein the 2D radiomic features are different from the 3D radiomic features;

excluding from the set of 3D radiomic features redundant radiomic features based on a comparison of the 3D radiomic features and 2D features;

in response to the exclusion, extracting a selected set of radiomic features from the 3D radiomic features;

obtaining, using one or more processors, a second plurality of 2D medical images captured at a second time period different from the first time period, performing, using the one or more processors, target tissue detection and target tissue segmentation for each the second plurality of 2D medical images to produce a set of segmented target tissue images, and generating, using the one or more processors, a second 3D model of detected and segmented target tissue;

identifying, using the one or more processors, the selected set of radiomic features in the second 3D model; and comparing, using the one or more processors, the selected set of radiomic features in the first 3D model and the second 3D model and determining a change in the set of radiomic features.

29. The method of claim 28, wherein first time period is before a tumor therapy and the second time period is after the tumor therapy.

30. The method of claim 29, further comprising determining a tumor treatment effectiveness from the comparison of the set of radiomic features in the first 3D model and the second 3D model.

31. The method of claim 28, wherein identifying the set of radiomic features in the first 3D model and/or identifying the set of radiomic features in the second 3D model comprises:

identifying a master set of radiomic features;

extracting a selected set of radiomic features from the first 3D model and/or the second 3D model; and identifying from among the selected set of radiomic features, radiomic features that are significantly associated with clinical outcomes and/or genomic data.

\* \* \* \* \*